United States Patent
Aguilar

(10) Patent No.: US 11,857,549 B2
(45) Date of Patent: Jan. 2, 2024

(54) COMPOSITIONS AND METHODS FOR THE TREATMENT OF LOWE SYNDROME

(71) Applicant: Purdue Research Foundation, West Lafayette, IN (US)

(72) Inventor: Ruben Claudio Aguilar, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 190 days.

(21) Appl. No.: 17/370,676

(22) Filed: Jul. 8, 2021

(65) Prior Publication Data
US 2022/0079941 A1 Mar. 17, 2022

Related U.S. Application Data

(60) Provisional application No. 63/079,536, filed on Sep. 17, 2020.

(51) Int. Cl.
| | | |
|---|---|---|
| *C07D 498/18* | (2006.01) | |
| *A61K 31/436* | (2006.01) | |
| *A61K 31/505* | (2006.01) | |
| *A61P 3/00* | (2006.01) | |

(52) U.S. Cl.
CPC .......... *A61K 31/505* (2013.01); *A61K 31/436* (2013.01); *A61P 3/00* (2018.01)

(58) Field of Classification Search
CPC .. C07D 498/18; A61K 31/436; A61K 31/505; A61P 3/00
See application file for complete search history.

(56) References Cited

PUBLICATIONS

Choudhury, R. et al., Lowe Syndrome Protein OCRL1 Interacts with Clathrin and Regulates Protein Trafficking between Endosomes and the Trans-Golgi Network, Molecular Biology of the Cell, 16, pp. 3467-3479, 2005.
Coon, B. et al., Lowe syndrome patient fibroblasts display Ocrl1-specific cell migration defects that cannot be rescued by the homologous Inpp5b phosphatase, Human Molecular Genetics, 18, pp. 4478-4491, 2009.
Coon, B et al., The Lowe syndrome protein OCRL1 is involved in primary cilia assembly, Human Molecular Genetics, 21, pp. 1835-1847, 2012.
Lasne, D. et al., Bleeding disorders in Lowe syndrome patients: evidence for a link between OCRL mutations and primary haemostasis disorders, British Journal of Haematology, 150, pp. 685-688, 2010.
Madhivanan, K. et al., Lowe syndrome. Between primary cilia assembly and Rac1-mediated membrane remodeling, Communicative & Integrative Biology, 5, pp. 641-644, 2012.
Madhivanan, K. et al., Role of Ocrl1 in Primary Cilia Assembly, International review of cell and molecular biology, 317, pp. 331-347, 2015.
Madhivanan, K. et al., Lowe syndrome patient cells display mTOR- and RhoGTPase-dependent phenotypes alleviated by rapamycin and statins, Human Molecular Genetics, vol. 00, pp. 1-16, 2020.
Mehta, Z. et al., The Cellular and Physiological Functions of the Lowe Syndrome Protein OCRL1, Traffic, 15, pp. 471-487, 2014.
Oltrabella, F. et al., The Lowe Syndrome Protein OCRL1 Is Required for Endocytosis in the Zebrafish Pronephric Tubule, PLOS Genetics, 10.1371, pp. 1-24, 2015.
Pirruccello, M. et al., Inositol 5-phosphatases: insights from the Lowe syndrome protein OCRL, Trends in Biochemical Sciences, 37, pp. 134-143, 2012.
Suchy, S. et al., The Deficiency of PIP2 5-Phosphatase in Lowe Syndrome Affects Actin Polymerization, Am. J. Hum. Genet., 71, pp. 1420-1427, 2002.
Van Rahden, V. et al., The 5-phosphatase OCRL mediates retrograde transport of the mannose 6-phosphate receptor by regulating a Rac1-cofilin signalling module, Human Molecular Genetics, 21, pp. 5019-5038, 2012.

*Primary Examiner* — Brenda L Coleman
(74) *Attorney, Agent, or Firm* — Purdue Research Foundation

(57) ABSTRACT

A combination of active agents for the treatment of Lowe Syndrome (LS) comprising a RhoA inhibitor and a mTOR inhibitor; a pharmaceutical composition comprising the combination and a pharmaceutically acceptable carrier; a combination of pharmaceutical compositions in which one composition comprises a RhoA inhibitor and the other composition comprises a mTOR inhibitor; and a method of treating a patient for LS.

5 Claims, 11 Drawing Sheets

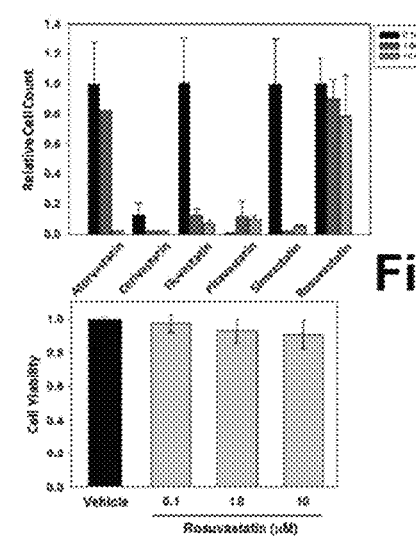
Fig. 2D

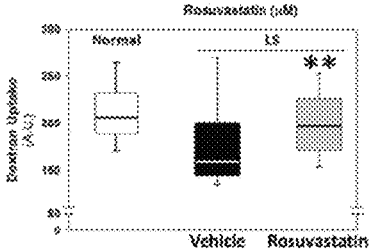
Fig. 2F
Fig. 2

COMPOSITIONS AND METHODS FOR THE TREATMENT OF LOWE SYNDROME

CROSS REFERENCE TO RELATED APPLICATION

This application claims priority to U.S. provisional patent application No. 63/079,536, which was filed Sep. 17, 2020, and which is hereby incorporated by reference in its entirety.

STATEMENT OF GOVERNMENT FUNDING

This invention was made with government support under DK109398 and TR002529 awarded by the National Institutes of Health. The government has certain rights in the invention.

TECHNICAL FIELD

The present disclosure relates to RhoA (Ras homolog family member A) inhibitors, statins (such as rosuvastatin), mTOR inhibitors (such as rapamycin), pharmaceutical compositions comprising the same, and methods of using the pharmaceutical compositions to treat Lowe Syndrome.

BACKGROUND

Lowe Syndrome (LS) is a devastating genetic disease caused by mutations in the OCRL1 (oculo-cerebro-renal syndrome of Lowe; OMIM #309000) gene on the X chromosome, which causes functional deficiencies of the inositol 5-phosphatase Ocrl1 (EC 3.1.3.36) that unfortunately lead to early death. Affected individuals have ocular, neurological and renal abnormalities. Affected individuals are born with bilateral cataracts. The most common cause of death is renal failure. It is unknown how OCRL1 mutations lead to LS, and there is no cure. And, while the disease is rare, it is estimated to affect tens of thousands of children worldwide.

Given its enzymatic activity, lack of Ocrl1 function leads to cellular accumulation of its preferred substrate—phosphatidyl-inositol (4,5) bisphosphate ($PI(4,5)P_2$) (Mehta et al., Traffic 15: 471-487 (2014)). The substrate accumulation affects trafficking (e.g., recycling (Choudhury et al., Mol Biol Cell 16: 3467-3479 (2005); van Randen et al., Hum Mol Genet 21: 5019-5038 (2012)) and signaling (e.g., regulation of actin polymerization (Suchy et al., Am J Hum Genet 71: 1420-1427 (2002)). Given that Ocrl1 has several interaction partners (Mehta et al. (2014), supra; Pirruccello et al., Trends Biochem Sci 37: 134-143 (2012)), it is likely that these partners mediate other functions that are predicted to impact trafficking and signaling.

Although LS was described for the first time more than 60 years ago and the gene was identified more than 20 years ago, no specific treatment is available for affected children. Using cells from affected children, two categories of phenotypes that shed light on the cellular basis of the disease have been identified (Coon et al., Hum Mol Genet 18: 4478-4491 (2009); Coon et al., Hum Mol Genet 21: 1835-1847 (2012); Madhivanan et al., Commun Integr Biol 5: 641-644 (2012); and Madhivanan et al., Int Rev Cell Mol Biol 317: 331-347 (2015)). One category involves membrane remodeling abnormalities. The other category involves primary cilia defects.

It has been discovered that the category of phenotypes involving membrane remodeling is characterized by fibroblasts with significant deficiencies in cell migration, spreading and fluid-phase uptake (FPU) as compared to normal cells (Coon et al. (2009), supra; Oltrabella et al., PLoS Genet 10.1371/journal.pgen.1005058 (Apr. 2, 2015)). FPU defects are believed to account for some of the kidney manifestations observed in LS patients. The role of Ocrl1 in membrane remodeling requires phosphatase activity and interaction with the endocyte machinery (AP2 and clathrin) (Coon et al. (2009), supra). RhoGTPase signaling mis-regulation (hyperactivation of RhoA and hypoactivation of Rac1) with Ocrl1 deficiency is the likely cause (van Randen et al. (2012), supra; Madhivanan et al. (2012), supra; Lasne et al., Br J Haematol 150: 685-688 (2010)).

The other category involves a deficiency in primary cilia assembly (Coon et al. (2012), supra). It is independent of membrane remodeling and reflects vesicle trafficking defects due to abnormal Ocrl1 phosphatase activity or lack of binding to the endosomal proteins Appl1-IPIP27/Ses5 (Coon et al. (2012), supra). Given the impact of primary cilia in renal function, this phenotype is also believed to contribute to patient kidney problems.

Both categories of phenotypes have been observed in a zebrafish model of LS. The observation underscores the relevance of both phenotypes to disease. Given that two independent Ocr1 functions are involved in LS, a single compound has yet to be identified that can revert both phenotypes.

In view of the above, there remains a need for a composition and a method of treatment of LS. It is an object of the present disclosure to provide a combination of active agents, a composition comprising same, and a method of using the combination or composition to treat Lowe Syndrome. This and other objects and advantages, as well as inventive features, will become apparent from the detailed description provided herein.

BRIEF SUMMARY

A combination of active agents for the treatment of Lowe Syndrome (LS) is provided. In an embodiment, the combination comprises a Ras homolog family member A (RhoA) inhibitor and a mTOR inhibitor in amounts sufficient to treat LS therapeutically. The RhoA inhibitor can be a spatial regulation inhibitor, such as a statin, a prenylation inhibitor, or a combination thereof. The statin can be rosuvastatin. The mTOR inhibitor can be rapamycin.

Also provided is a pharmaceutical composition. In an embodiment, the pharmaceutical composition comprises a RhoA inhibitor and a mTOR inhibitor in amounts sufficient to treat LS therapeutically and a pharmaceutically acceptable carrier. The RhoA inhibitor can be a spatial regulation inhibitor, such as a statin, a prenylation inhibitor, or a combination thereof. The statin can be rosuvastatin. The mTOR inhibitor can be rapamycin.

Further provided is a combination of pharmaceutical compositions. In an embodiment, a first pharmaceutical composition comprises a RhoA inhibitor in an amount sufficient to treat LS therapeutically and a pharmaceutically acceptable carrier and a second pharmaceutical composition comprises a mTOR inhibitor in an amount sufficient to treat LS therapeutically and a pharmaceutically acceptable carrier. The RhoA inhibitor can be a spatial regulation inhibitor, such as a statin, a prenylation inhibitor, or a combination thereof. The statin can be rosuvastatin. The mTOR inhibitor can be rapamycin. The combination of first and second pharmaceutical compositions can be formulated to be administered by the same or different routes. The combination of pharmaceutical compositions can be formulated to be administered at the same or different times.

Still further provided is a method of treating a patient for LS. In an embodiment, the method comprises administering to the patient a combination of a RhoA inhibitor and a mTOR inhibitor in amounts sufficient to treat LS therapeutically. In another embodiment, the method comprises administering to the patient a pharmaceutical composition comprising a RhoA inhibitor and a mTOR inhibitor in amounts sufficient to treat LS therapeutically and a pharmaceutically acceptable carrier. In yet another embodiment, the method comprises administering to the patient a combination of pharmaceutical compositions. One pharmaceutical composition comprises a RhoA inhibitor in an amount sufficient to treat LS therapeutically and a pharmaceutically acceptable carrier. The other pharmaceutical composition comprises a mTOR inhibitor in an amount sufficient to treat LS therapeutically and a pharmaceutically acceptable carrier. The combination of pharmaceutical compositions can be formulated to be administered by the same or different routes. The combination of pharmaceutical compositions can be formulated to be administered at the same or different times. Regarding the various embodiments of the method, the RhoA inhibitor can be a spatial regulation inhibitor, such as a statin, a prenylation inhibitor, or a combination thereof. Further regarding the various embodiments of the method, the statin can be rosuvastatin. Still further regarding the various embodiments of the method, the mTOR inhibitor can be rapamycin.

BRIEF DESCRIPTION OF THE FIGURES

FIG. 2. Statins ameliorate LS membrane remodeling phenotypes.

FIG. 2C, FIG. 2D and FIG. 2E. LS patient cells were treated with the indicated statins at the indicated concentration and processed in the following ways: fixed and stained with FITC-phalloidin/DAPI (FIG. 2C), used for viability assays either by staining/cell counting (upper panel) or by MTT assays (lower panel) (FIG. 2D), and for uptake of fluorescent-Cho, with and without (control) statins (FIG. 2E).

FIG. 2F. Fluid phase uptake was estimated on normal and LS cells treated as indicated, incubated with fluorescent-dextran, fixed, imaged and the fluorescent intensity associated with cells measured using ImageJ software (NIH). Statistical significance of the LS fluid-phase uptake phenotype difference between cells treated with vehicle or rosuvastatin was assessed by using the Wilcoxon test (**: $p<0.05$).

FIG. 3A and FIG. 3B: Normal and LS patient cells (treated with vehicle or rosuvastatin, Rsv) were seeded on fibronectin-coated surfaces. Cells adhered (FIG. 3A) or in suspension (FIG. 3B) were quantified as a function of time. Results represent the average of three independent experiments.

FIG. 3C and FIG. 3D: Normal and LS patient cells were subjected to fluid sheer stress and the fraction of detaching (FIG. 3C) and of cells that remain attached (FIG. 3D) were calculated by analyzing time-lapse microscopy data (FIG. 3C) and fixed/phalloidin-stained samples (FIG. 3D). Differences between normal and LS distributions were assessed by the Wilcoxon test (**: $p<0.05$).

FIG. 3E and FIG. 3F: Status of focal adhesions in Normal and LS patient cells was investigated by immunostaining with anti-phosphorylated FAK (FIG. 3E, left) and anti-vinculin (FIG. 3F, top) antibodies. Cells were imaged and the indicated adhesion structures were quantified as described (FIG. 3E, right, and FIG. 3F, bottom). White arrows: properly actin-linked vinculin structures; Red arrows: actin filaments disconnected from vinculin structures; Yellow arrows: vinculin-positive adhesions not linked to the actin cytoskeleton. **$p<0.05$ by the Wilcoxon test. Scale bars: 10 µm.

FIG. 5A. As described before, LS patient cells display primary cilia assembly defects (cilia length and number of ciliated cells under serum-starvation conditions) as compared to their normal counterparts. LS cilia assembly phenotypes were ameliorated by treatment with rapamycin (Rapa). **$p<0.05$ by the Wilcoxon test.

FIG. 5B. LS patient cells showed moderate decrease in cell viability as detected by MTT assays due to rapamycin treatment (at the indicated concentration) as compared to vehicle-treated cells.

FIG. 5C. Scheme depicting targets of inhibition by rapamycin on the mTOR pathway downstream of PIP2 (PI3K substrate) accumulation typical of LS patient cells.

FIG. 5D. Levels of activated (phosphorylated) elements of the PI3K/mTOR pathway were detected by Western blotting with specific antibodies on lysates from normal and LS patient cells treated with vehicle (DMSO) or rapamycin. The total protein content of each protein investigated and tubulin (loading control) were also determined.

FIG. 5E. Upper panel: Effect of alternative mTOR inhibitors on the ciliogenesis by LS patient cells as compared to vehicle-treated cells. In contrast to vehicle and SAR405 (inhibitor of the mTOR-independent PI3KcIII), mTOR inhibitors WYE132 and INK128 were able to ameliorate the LS ciliogenesis phenotype. Phenotype. **p<(0.05/3) (Bonferroni correction) by the student's t-test test. Lower panel: hyperactivation of mTOR was suppressed by mTOR inhibitors WYE132 (WYE) and INK128 (INK), but not by Vehicle (V) or SAR405 (SAR). NS: non-significant.

FIG. 8A: LS cells from a patient (LS2) different than the one characterized in FIG. 1 were treated with the indicated pharmacological agents or vehicle and cell size distribution was determined and compared to the one from cells from a normal individual (same as in FIG. 1). Rsv: rosuvastatin; Rapa: rapamycin.

FIG. 8B: Human HK2 kidney cells wild-type (WT) and OCRL1 knock-out (K.O.) were treated or not with a RhoA inhibitor and cell spreading experiments were conducted as in FIG. 1. Significance of differences among distributions was statistically assessed using the KS test. Bonferroni correction for multiple comparisons was applied (**p<(0.05/2=0.025)): LS samples vehicle-treated vs drug-treated (FIG. 8A) and HK2 OCRL1 K.O. vs WT cells (FIG. 8B).

FIG. 8C: LS patient cells were treated with vehicle (V), pitavastatin (Ptv) or rosuvastatin (Rsv) at the indicated concentrations and times. NS: non-significant.

FIG. 10A. HK2 WT and OCRL1 K.O were seeded in fibronectin-coated surfaces and analyzed as in FIG. 3A (upper panel) and FIG. 3E (lower panel). FIG. 10B. Serum-starved cells were processes as described and as in FIG. 5A. Statistical significance of the difference between WT and K.O. cells was assessed by student t-test and Wilcoxon test (Upper panel, and lower panel, respectively; **p<0.05).

DETAILED DESCRIPTION

Figure 1:
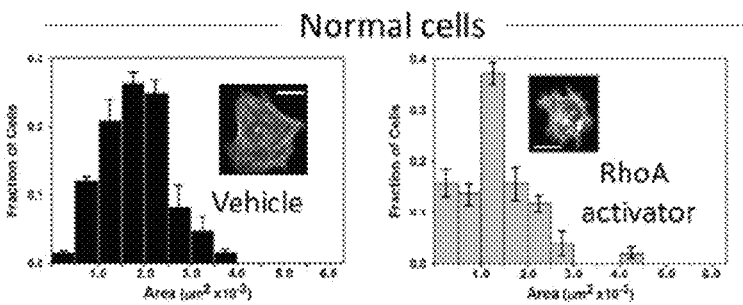
FIG. 1. LS cell spreading phenotype is affected by RhoGTPase modulators. Normal (FIG. 1A) and LS patient (FIG. 1B) cells were resuspended and treated with vehicle or the indicated pharmacological agent as indicated. Thirty minutes after seeding on fibronectin-coated surfaces the cells were fixed, stained with rhodamine-phalloidin, and imaged. The areas of at least 200 cells (in at least 3 experiments) were measured using ImageJ software (National Institutes of Health, Bethesda, MD, USA) and size-distribution histograms were constructed. Insets show examples of stained cells representative of the high frequency groups within each histogram. Scale bar: 10 µm. **$p<(0.05/4=0.0125)$ (Bonferroni correction) by the KS test. LS patient cells (FIG. 1C) were also resuspended and treated with two important RhoA effectors—Rho-associated kinase (ROCK) and myosin light chain kinase (MLCK), while also using an inhibitor of p21 activated kinase (PAK), which acts downstream of Cdc42/Rac1, as a control. Cells were seeded, fixed, stained, and imaged and size-distribution histograms were constructed as described above. NS: non-significant.
Figure 1:
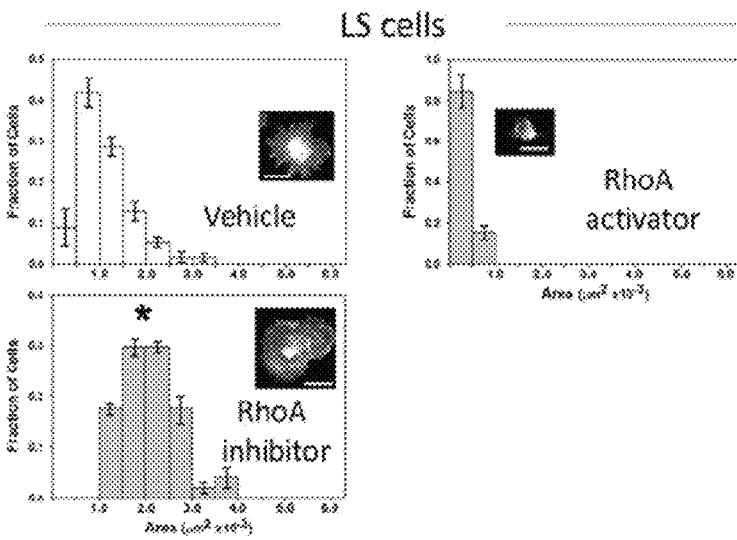
Figure 1:
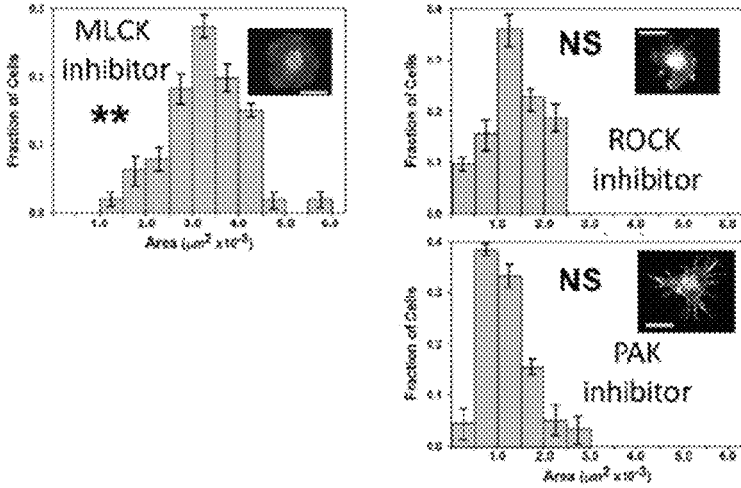

The present disclosure is predicated on the discovery of a combination of active agents that treats two important signaling pathways affected in patients with Lowe Syndrome (LS). RhoGTPase signaling abnormalities lead to cell migration, cell spreading and fluid-phase uptake (FPU) defects, and PI3K/mTOR hyperactivation interferes with primary cilia assembly. The combination of active agents comprises (i) a RhoA (Ras homolog family member A) inhibitor (e.g., a spatial regulation inhibitor or a prenylation inhibitor), a statin, or a combination thereof and (ii) a mTOR inhibitor. The combination can include FDA-approved drugs. One FDA-approved active agent is a class of drugs called statins. Statins mitigate adhesion and spreading abnormalities. The other FDA-approved active agent is rapamycin. Rapamycin facilitates ciliogenesis. No single drug has been discovered to alleviate both phenotypes.

In view of the above, provided is a combination of active agents for the treatment of LS. In an embodiment, the combination comprises a Ras homolog family member A (RhoA) inhibitor and a mTOR inhibitor in amounts sufficient to treat LS therapeutically. The RhoA inhibitor can be a spatial regulation inhibitor. The combination can include FDA-approved drugs.

Spatial regulation inhibitors of RhoGTPase interfere with the localization of RhoGTPase on the surface of cell membranes. Examples include statins and prenylation inhibitors. Thus, the combination can comprise a statin, a prenylation inhibitor, or a combination thereof.

Statins are a class of lipid-lowering drugs. They are the most common cholesterol-lowering drugs and help reduce illness and mortality in those who are at high risk of cardiovascular disease. They inhibit or block an enzyme called HMG-CoA reductase (3-hydroxy-3-methylglutaryl coenzyme A reductase), which is involved in the synthesis of mevalonate, which plays a role in sterol synthesis, including cholesterol synthesis. Any suitable statin can be used in the method. Examples of statins include, but are not limited to, atorvastatin, cerivastatin, fluvastatin, lovastatin, pitavastatin, pravastatin, rosuvastatin, and simvastatin. A statin should be selected for high efficacy and low toxicity. An example of such a statin is rosuvastatin. Other statins, such as pitavastatin, simvastatin, and cerivastatin are less efficacious and more toxic.

Prenylation inhibitors inhibit the addition of prenyl groups to RhoGTPase. An example includes geranylgeranyl transferase 1 (GGTase-1) inhibitors (GGTIs). GGTIs comprise a variety of small molecules. One example is P61A6, which has a dihydropyrrole ring as its core scaffold. It inhibits geranylgeranylation without affecting farnesylation and has a remarkably long plasma half-life. Another example is GGTI-2418, which is also known as PTX100 (Prescient Therapeutics) and is currently in phase I clinical trials for the treatment of cancer and solid tumors.

mTOR inhibitors inhibit mTOR, a kinase that plays a fundamental role in regulating the progression of the cell cycle. An example is rapamycin, which is also called sirolimus. Rapamycin is an immunosuppressive drug that was found in soil bacteria (*Streptomyces hygroscopicus*) collected on Easter Island in the 1960's. The drug's name comes from the island's native name—Rapa Nui. The drug is used in the prevention of transplant rejection. Rapamycin suppresses immune response by inhibiting the activation and proliferation of T cells. It acts specifically by binding to FK-binding protein 12 (FKBP12). The rapamycin-FKBP12 complex then binds to the mammalian target of rapamycin—mTOR.

When the rapamycin-FKBP12 complex binds to mTOR, it inhibits mTOR. The inhibition of mTOR disrupts cell division and the proliferation of T cells.

In view of the above, also provided is a pharmaceutical composition. In an embodiment, the pharmaceutical composition comprises (i) a RhoA inhibitor and (ii) a mTOR inhibitor in amounts sufficient to treat LS therapeutically and a pharmaceutically acceptable carrier. The RhoA inhibitor can be a spatial regulation inhibitor, such as a statin, a prenylation inhibitor, or a combination thereof. The statin can be rosuvastatin. The mTOR inhibitor can be rapamycin.

Further provided is a combination of pharmaceutical compositions. In an embodiment, one pharmaceutical composition comprises a RhoA inhibitor in an amount sufficient to treat LS therapeutically and a pharmaceutically acceptable carrier. The other pharmaceutical composition comprises a mTOR inhibitor in an amount sufficient to treat LS therapeutically and a pharmaceutically acceptable carrier. The RhoA inhibitor can be a spatial regulation inhibitor, such as a statin, a prenylation inhibitor, or a combination thereof. The statin can be rosuvastatin. The mTOR inhibitor can be rapamycin. The combination of pharmaceutical compositions can be formulated to be administered by the same or different routes. The combination of pharmaceutical compositions can be formulated to be administered at the same or different times.

Any suitable statin can be used in the pharmaceutical composition. Examples of statins include, but are not limited to, atorvastatin, cerivastatin, fluvastatin, lovastatin, pitavastatin, pravastatin, rosuvastatin, and simvastatin. A statin should be selected for high efficacy and low toxicity. An example of such a statin is rosuvastatin. Other statins, such as pitavastatin, simvastatin, and cerivastatin are less efficacious and toxic.

Any suitable prenylation inhibitor can be used in the pharmaceutical composition. Examples of prenylation inhibitors include, but are not limited to, GGTIs, such as P61A6 and GGTI-2418, which is also known as PTX100.

The use of statins, in particular rosuvastatin, can be preferred over prenylation inhibitors due to the prevalent use and general safety of statins. Rosuvastatin can be a preferred choice of statin due to its efficacy and low toxicity.

The formulation of a pharmaceutical composition is known in the art. The active agents in the combination can be administered separately to a patient, such as in the form of separate pharmaceutical compositions. When administered separately, the active agents, or pharmaceutical compositions comprising the separate active agents, can be administered simultaneously or sequentially, in either order, as deemed appropriate for the patient by a healthcare provider. If desired, the active agents, combination of active agents, pharmaceutical compositions comprising the separate active agents, or a pharmaceutical composition comprising the combination of active agents can be provided in a kit, such as a blister pack of oral dosage forms.

Carriers, excipients and other additives commonly used for pharmaceutical compositions can be used to prepare pharmaceutical compositions comprising the separate active agents (or pharmaceutically acceptable salts thereof) or combination of active agents (or pharmaceutically acceptable salts thereof) for use in the method of treating a patient for LS. Examples of inert excipients include, but are not limited to, lactose, mannitol, glucose, hydroxypropylcellulose, microcrystalline cellulose, starch, polyvinylpyrrolidone, magnesium aluminum silicate, and the like. Other inert ingredients include, but are not limited to, lubricants, such as magnesium stearate, disintegrating agents, such as sodium carboxymethyl starch, and dissolution aids.

Commercially available compositions, or modifications thereof, including combinations thereof, can be used in the method. Indeed, there are perfectly standardized formulations for rapamycin and statins, such as rosuvastatin, currently available. The formulation will depend, in part, on the route of administration.

Forms of administration include those suitable for oral administration of statins, such as rosuvastatin, and rapamycin, and may include forms such as tablets, pills, capsules, granules, powders, emulsions, syrups, solutions, aqueous or oily suspensions, elixirs, and other liquid preparations. Such liquid preparations can include diluents, such as water or alcohol (which can be contra-indicated in the very young), solubilizing agents, wetting agents, suspending agents, sweeteners, flavoring agents, and preservatives. If necessary or desired, tablets and pills can be coated with sugar, a gastric/enteric coating agent, and the like.

Other forms of administration include those suitable for non-oral administration of statins, such as rosuvastatin, and rapamycin, and may include forms such as forms suitable for administration by intravenous injection or infusion, subcutaneous or intramuscular injection, suppository, transdermal implant, or inhalation. Injections for parenteral administration can include sterile aqueous or non-aqueous liquid preparations, suspensions, and emulsions. Diluent aqueous solutions can include distilled water and physiological saline. Non-aqueous diluent solutions can include propylene glycol, polyethylene glycol, vegetable oils, alcohols (which can be contra-indicated in the very young), and polysorbate 80. Such compositions can further contain isotonic agents, such as preservatives, wetting agents, emulsifying agents, dispersing agents, stabilizing agents, dissolving aids, and the like. The compositions can be sterilized by filtration, addition of anti-bacterial agents, or irradiation, for example. In addition, these compositions can be made as sterile, solid compositions and dissolved or suspended in sterile water/solvent for injection prior to use. Compositions for transmucosal administration, such as inhalation and nasal absorption, can be solid, liquid, or semi-solid, and can be made in accordance with conventional methods. For example, excipients such as lactose, starch, pH adjusting agents, preservatives, surfactants, lubricants, stabilizing agents, thickening agents, and the like can be added. A suitable inhalation or insufflation device can be used. Examples of such devices include metered dose inhalers and pressurized aerosol spray canisters, which contain a suitable propellant, such as chlorofluoroalkane, hydrofluoroalkane, carbon dioxide, or the like.

Appropriate dosages can be determined in accordance with dosage range-finding techniques known in the art. FDA-approved dosages for rapamycin and statins, such as rosuvastatin, can be used when appropriate for the patient being treated. Rapamycin is known to have a narrow therapeutic index and a wide interpatient variability, making therapeutic drug monitoring necessary. In children, clearance is reportedly most associated with body size parameters (body surface area and weight). Age reportedly also affects clearance in very young children; it is hypothesized that this may be due to changes in drug absorption and metabolism as children mature. See, e.g., Scott et al., Ther Drug Monitor 35(3): 332-337 (June 2013).

Generally speaking, a daily dose of an active agent administered orally to adult patients can range from about 0.001 mg/kg to 100 mg/kg, whereas a daily dose of an active agent administered intravenously can range from about 0.001 mg/kg to 10 mg/kg. The daily dose can be given in a single dose or divided into 2-4 doses. Fewer doses, such as a single dose, are possible with extended-release formulations. A daily dose of an active agent administered to a child, a toddler, an infant, a newborn, or a pre-term baby will be substantially less than a daily dose of an active agent administered to an adult.

Still further provided is a method of treating a patient for LS. In an embodiment, the method comprises administering to the patient a combination of a RhoA inhibitor and a mTOR inhibitor in amounts sufficient to treat LS therapeutically. In another embodiment, the method comprises administering to the patient a pharmaceutical composition comprising a RhoA inhibitor and a mTOR inhibitor in amounts sufficient to treat LS therapeutically and a pharmaceutically acceptable carrier. In yet another embodiment, the method comprises administering to the patient a combination of pharmaceutical compositions. One pharmaceutical composition comprises a RhoA inhibitor in an amount sufficient to treat LS therapeutically and a pharmaceutically acceptable carrier. The other pharmaceutical composition comprises a mTOR inhibitor in an amount sufficient to treat LS therapeutically and a pharmaceutically acceptable carrier.

The combination of pharmaceutical compositions can be formulated to be administered by the same or different routes. Any suitable route or routes (e.g., the active agents of the combination can be administered by the same or different routes) of administration can be used. In this regard, the route(s) of administration can depend, in part, on the age of the patient, such that certain routes may be preferred for pre-term babies and newborns over the routes used for administration to infants, toddlers, and young children. For example, intravenous administration may be preferred for pre-term babies and newborns, whereas injections or liquid formulations suitable for oral administration may be preferred for infants, toddlers, and young children. The combination of pharmaceutical compositions can be formulated to be administered at the same or different times.

Regarding the various embodiments of the method, the RhoA inhibitor can be a spatial regulation inhibitor, such as a statin, a prenylation inhibitor, or a combination thereof. Further regarding the various embodiments of the method, the statin can be rosuvastatin. Still further regarding the various embodiments of the method, the mTOR inhibitor can be rapamycin.

EXAMPLES

The following examples serve to illustrate the present invention and are not intended to limit the scope of the claimed invention in any way.

Reagents

Materials were purchased from Fisher Scientific (Fairlawn, NJ) or Sigma (St. Louis, MO) unless stated otherwise. The different active agents and antibodies used are set forth in Tables 1 and 2, respectively.

TABLE 1

Pharmacological agents used

| Compound | Activity | Source | Catalog number | Use (conc/time) |
|---|---|---|---|---|
| calpeptin | Rho activator | Cytoskeleton, Inc | CN01 | 137.5 µM/1 h |
| C3 transferase | Rho inhibitor | Cytoskeleton, Inc | CT04 | 10.5 nM/2 h (Fibroblasts), 4.2 nM/2 h (HK2) 4.2 nM/2 h (HK2) |
| fasudil | Rho kinase inhibitor | Selleck Chemicals | S1573 | 10 µM/3 h |
| PF-3758309 | PAK inhibitor | AdooQ Bioscience | A11930 | 1-10 µM/3-6 h |
| ML7 | MLCK inhibitor | Enzo LifeSciences | BML-EI197-0010 | 1 µM/6 h |
| fluvastatin | HMG-CoA reductase inhibitors | Cayman Chemicals | 10010337 | 1-100 µM/3-6 h |
| simvastatin | | Cayman Chemicals | 10010344 | 1-10 µM/8-12 h |
| atorvastatin | | Toronto Research Chemicals | A791750 | 1-100 µM/3-6 h |
| pitavastatin | | Selleck Chemicals | S1759 | 10 µM/12 h |
| rosuvastatin | | Bio Vision | 1955-5 | 100 µM/12 h or 10-20 µM/72 h (long-term exposure) |
| FTI276 | farnesylation inhibitor | CalBioChem | 344550 | 0.5 µM/6 h |
| rapamycin | mTOR inhibitor | Cayman Chemicals | No13346 | 100 nM/12 h or 10 nM/72 h (long-term exposure) |
| WYE132 | mTOR inhibitor | BioVision Inc | 2256-500 | 1 µM/72 h |
| INK128 | mTOR inhibitor | MedKoo Bioscience | 205495 | 20 nM/72 h |
| SAR405 | PI3K cIII inhibitor | MedChem Express | HY12481 | 1 µM/72 h |

TABLE 2

Antibodies

| Antigen | Host | Source | Dilution used and application[a] |
|---|---|---|---|
| mTOR (total) | rabbit | Cell Signaling (#2972) | 1:1000 (WB) |
| p-mTOR (S2448) | rabbit | Cell Signaling (#2971) | 1:1000 (WB) |
| p-mTOR (S2481) | rabbit | Cell Signaling (#2974) | 1:1000 (WB) |
| Akt (Total) | rabbit | Bioss (Bs-0115R) | 1:500 (WB) |
| p-Akt (S473) | rabbit | Cell Signaling (#4058) | 1:1000 (WB) |
| SGK-1 (Total) | rabbit | Millipore (# 07-315) | 1:100 (WB) |
| p-SGK-1 (S422) | mouse | Santa Cruz (sc-16745) | 1:100 (WB) |
| tubulin | mouse | Biolegend (627903) | 1:500 (WB) |
| acetylated tubulin | mouse | Sigma Aldrich (6-11B-1) | 1:1000 (IIF) |
| pericentrin | rabbit | Abcam (ab4448) | 1:300 (IIF) |
| vinculin | mouse | Sigma Aldrich (V9131) | 1:800 (IIF) |
| phospho-paxillin | rabbit | Epitomics (2128-1) | 1:500 (WB) |
| pan FAK | rabbit | Santa Cruz (C-20) | 1:500 (WB) |
| phospho-FAK | rabbit | Santa Cruz (11765-R) | 1:50 (IIF), 1:500 (WB) |
| LAMP2 | mouse | Santa Cruz (sc-18822) | 1:150 (IIF) |

[a]WB: Western blotting; IIF: Indirect Immuno-Fluorescence.

Cells and Culture Conditions

Normal (GM07492) and LS primary dermal fibroblasts (GM01676 and GM03265) were obtained from the NIHGMS Human Genetic Cell Repository (Coriell Institute for Medical Research, Camden, NJ, USA). Cells were maintained in Dulbecco's Modified Eagle Medium (DMEM), streptomycin/penicillin, 2 mM L-glutamine and 15% fetal bovine serum (FBS) at 37° C. in a 5% CO2 incubator. When needed, cells were transferred to fibronectin-coated surfaces (plates or coverslips) prepared by incubation with 10 µg/mL fibronectin for 2 h at 37° C. Normal human proximal tubule epithelial (HK2) and human embryonic kidney epithelial 293T (HEK293T) cells obtained from ATCC were grown in DMEM, streptomycin/penicillin, 2 mM L-glutamine and 10% FBS at 37° C. in a 5% CO2 incubator. OCRL1$^{-/-}$ (OCRL K.O) HK2 and HEK293T cells were prepared by GenScript, Inc., Piscataway, NJ, USA, and maintained under the same conditions as their normal counterparts. Characterization of these cell lines has been described before (Hsieh et al., PLoS One 10.1371/jounal.pone.0192635 (Feb. 14, 2018)).

Pharmacological Treatments and Viability/Toxicity Assessment

Cells were incubated with the indicated drugs for the specified times at different concentrations as described in low serum (0.1%) media to avoid substantial protein-mediated drug sequestration. In addition to cell counting post-treatment, a sample of cells seeded on fibronectin-coated coverslips was fixed and stained with fluorescein isothiocyanate (FITC)-phalloidin and DAPI (4',6-diamidino-2-phenylindole) for cell morphology inspection. Viability was monitored by performing MTT (3-(4,5-dimethylthiazol-2-yl)-2,5-diphenyltetrazolium bromide) assays as follows: Following treatment of cells (in triplicates) with indicated drugs at different concentrations for specified times, media were aspirated and replaced with MTT solution (freshly prepared at 0.5 mg/ml in complete media) and incubated for 1.5 h. Additionally, a blank control with only MTT reagent containing no cells was also prepared. Following incubation, solution was aspirated and MTT was immediately solubilized using 1 mL DMSO (dimethylsulfoxide) (per well) by gentle pipetting. Absorbance values of solubilized MTT solution from the different wells were measured at 570 nm using a spectrophotometer.

Cholesterol Uptake Assay

Assay for cholesterol uptake was performed using cholesterol-free media and an AbCam kit (ab236212; Cambridge, UK) according to manufacturer's instructions. During the timeframe of the assay no changes in morphology, adhesion or spread aspect of control cells were detected.

Cell Spreading Assays

Two approaches to monitor cell spreading were used: after a predetermined time-point and at multiple time points.

1) Spreading after a Predetermined Time-Point.

Human dermal fibroblasts (12 h after seeding) were treated with the indicated drug (or vehicle) in 0.1% serum for the indicated time. After drug treatment, the cells were lifted with 20 mM EDTA (ethylenediaminetetraacetic acid) in PBS (phosphate-buffered saline), pelleted at 300×g for 5 min and resuspended in 1% serum in the presence of drug or vehicle. Cell suspensions were then set in a rotator for 1 hour before seeding them on fibronectin-coated coverslips for 30 min, undisturbed, to allow attachment and spreading. After spreading, coverslips were gently rinsed with PBS and fixed in 4% formaldehyde for 10 min at room temperature. Cells were stained with rhodamine-phalloidin and imaged by epifluorescence microscopy. At least 50 cells were quantified per experiment by tracing and measuring cell areas by using the magic wand tool in ImageJ software (National Institutes of Health (NIH), Bethesda, MD, USA).

2) Spreading at Multiple Time Points.

Human dermal fibroblasts were treated as described above, seeded on fibronectin-coated LabTek chambers, and allowed to attach and spread. Cells were imaged at intervals of 10 min after seeding for 8 h using 20× objective in a Zeiss Axiovert inverted microscope. Number of detaching cells was quantified every 10 min up to the first hour by using the cell counter tool in ImageJ (NIH). To determine spreading kinetics, individual cells were tracked in each time lapse image and were scored from 1-5 based on general cell morphology. Briefly, cells that were just attached and looked circular with no protrusions or visible extensions received a score of 1. Cells with needle-like (filopodia) projections were scored 2, cells with lamellopodia-like extensions were scored 3, cells with more extended lamellopodia-like extensions and increased cell area were given a score of 4, and a further increase in cell area, often accompanied by isotropic spread morphology, was given a score of 5.

Alternatively, cells were treated as described above and allowed to attach on fibronectin-coated dishes. Immediately after seeding, the cells were imaged with a 10× objective simultaneously using up to 3 Cytosmart Imaging Systems (Lonza, Basel, Switzerland) at intervals of 30 s for 2 h. Number of cells attached was quantified every 10 min up to the first hour using the Cell Counter tool in ImageJ software (NIH).

Confocal Microscopy

Cells were prepared as described under "Spreading after a pre-determined time point." After fixation, indirect immunofluorescence was performed using antibodies against phospho-FAK (Y397) or vinculin. Briefly, cells were gently washed with PBS, fixed with 4% formaldehyde-PBS for 10 min and permeabilized using 0.25% Triton-X 100 in PBS for 20 min, followed by blocking with 5% BSA (bovine serum albumin) in PBS for 30 min. Cells were also immunostained with Phalloidin-FITC and DAPI to label the actin cytoskeleton and nucleus, respectively. Images were acquired at the Indiana O'Brien Center for Biological Microscopy (ICBM; Division of Nephrology, Indiana University School of Medicine, Indianapolis, IN, USA) using an Olympus IX81 inverted confocal microscope. A 60× Oil objective (NA 1.42) was used and randomly selected fields were imaged using constant voltage, gain and intensity for the different groups, as well as uniform step size (0.19 pin) using sequential image collection mode.

Fluid Shear Stress Assays

Two approaches to monitor resistance to Fluid sheer stress (FSS) were utilized: after a predetermined time-point and at multiple time points.

1) FSS after a Predetermined Time-Point.

Equal numbers of normal and LS cells were allowed to attach on fibronectin-coated coverslips (22 mm×22 mm) as described before. Twenty minutes after seeding, one set of coverslips was gently washed and immediately fixed using 4% formaldehyde. Another set of coverslips was subjected to fluid shear stress by flushing 1×PBS using a standard wash bottle with spout and then fixed with 4% formaldehyde. Coverslips were then immuno-stained with Rhodamine-Phalloidin (1:200) to label the actin cytoskeleton and with DAPI to label the nucleus. Cells were then imaged by using Axiovert inverted epifluorescence microscope. For each group, three random rows were selected on the coverslip and completely imaged from end to end without skipping any field within the row. Attached cells were then counted from each row and the fraction of cells remaining on the coverslips before and after fluid shear stress was calculated.

2) FSS at Multiple Time Points.

Normal and LS fibroblasts were seeded on fibronectin-coated wells and allowed to attach. Immediately after seeding, cells were imaged with a 10× objective simultaneously using up to three Cytosmart Imaging Systems (Lonza, Basel, Switzerland) at intervals of 30 s for up to 2 h. Twenty minutes after seeding, a pipette tip was used to gently aspirate 1 mL of media, which was immediately released into the culture dish to produce a sudden fluid shear stress. Numbers of cells attached before this event (t=19 min) and after the shear stress (t=24 min) were counted using the Cell Counter tool on ImageJ (NIH) and the fraction of cells detaching was calculated.

Fluid Phase Uptake Assay

Cells were seeded on glass coverslips for 12 h prior to experiments and then treated with the indicated drug or vehicle in 0.1% serum media for the specific amount of time. Cells were then incubated with 1 mg/mL 70 kDa dextran-TMR (tetramethyl rhodamine) in complete media containing FBS at 37° C. for 20 min. Coverslips were cooled to 4° C. in PBS and washed extensively for 5 min before fixation. The cells were then imaged and the fluorescence intensity of the dextran-TMR taken up by cells was measured using Image J (NIH).

Ciliogenesis Assays

Cells were seeded on glass cover slips and grown for 24 h in complete media. Then media was replaced by 0.1% serum DMEM (starvation media) containing vehicle or the drug to induce ciliogenesis for the indicated times. Cells were then fixed in 4% formaldehyde-PBS for 10 min and immuno-labeled with anti-acetylated tubulin antibody (see Table 2). At least 50 cells were imaged for every experiment and experiments were repeated at least thrice. The fraction of cells displaying cilia and cilia length were determined as described previously (Coon et al. (2012), supra).

Indirect Immunofluorescence for Lysosomes

Following treatment with drugs, cells were washed and fixed with 4% formaldehyde-PBS for 10 min and immune-labeled for LAMP2 (lysosome-associated membrane protein 2). Random fields were imaged using a Zeiss Axiovert inverted microscope using a 40× objective with constant fluorescence exposure times. Cells were scored for the presence or absence of autolysosomes and the fraction of cells/field exhibiting these structures was determined.

Western Blotting

Normal and LS cells were seeded on 100 mm plates and grown to 60-70% confluency in complete media. Then media was exchanged with 0.1% serum DMEM media with DMSO or 10 nM rapamycin for 12 hrs. The cells were washed twice with ice-cold PBS, collected by scraping cells in 200 µl/plate of lysis buffer (25 mM HEPES-KOH, pH7.4, 250 mM NaCl, 1% Triton-X-100 supplement with phosphatase and protease inhibitors), and lysed by passing the cells 10 times through a 26G1/2 needle. The lysates were centrifuged at 14,000×g for 20 min at 4° C., and the supernatant fractions were collected. The samples were analyzed by SDS-PAGE using 7% or 10% polyacrylamide gels and transferred to nitrocellulose membranes. The membranes were blocked with 5% skim milk in PBST (1× phosphate-buffered saline with Tween® detergent) and immunoblotted with the indicated primary and HRP-conjugated secondary antibodies.

Statistical Analysis

Statistical significance of differences between spreading-distribution histograms was analyzed using the Kolmogorov-Smirnov (KS) test. While the student's t-test was used to evaluate the significance of differences of normally distributed samples, the Wilcoxon's test was employed when samples were non-normally distributed. In all cases, the Bonferroni's correction for multiple comparisons was performed whenever applicable [$\alpha C = p/n$; n being the number of comparisons]. After carefully analyzing each data set distribution the most appropriate representation in each case was adopted. These representations included histograms, box plots and scatter data as they allow thorough examination of the data distribution (Taylor, *An Introduction to Error Analysis*, University Science Books, Sausalito, CA (1997)). When the data presented a normal distribution, a bar graph with standard deviations as visualization strategy was used.

Figure 3:
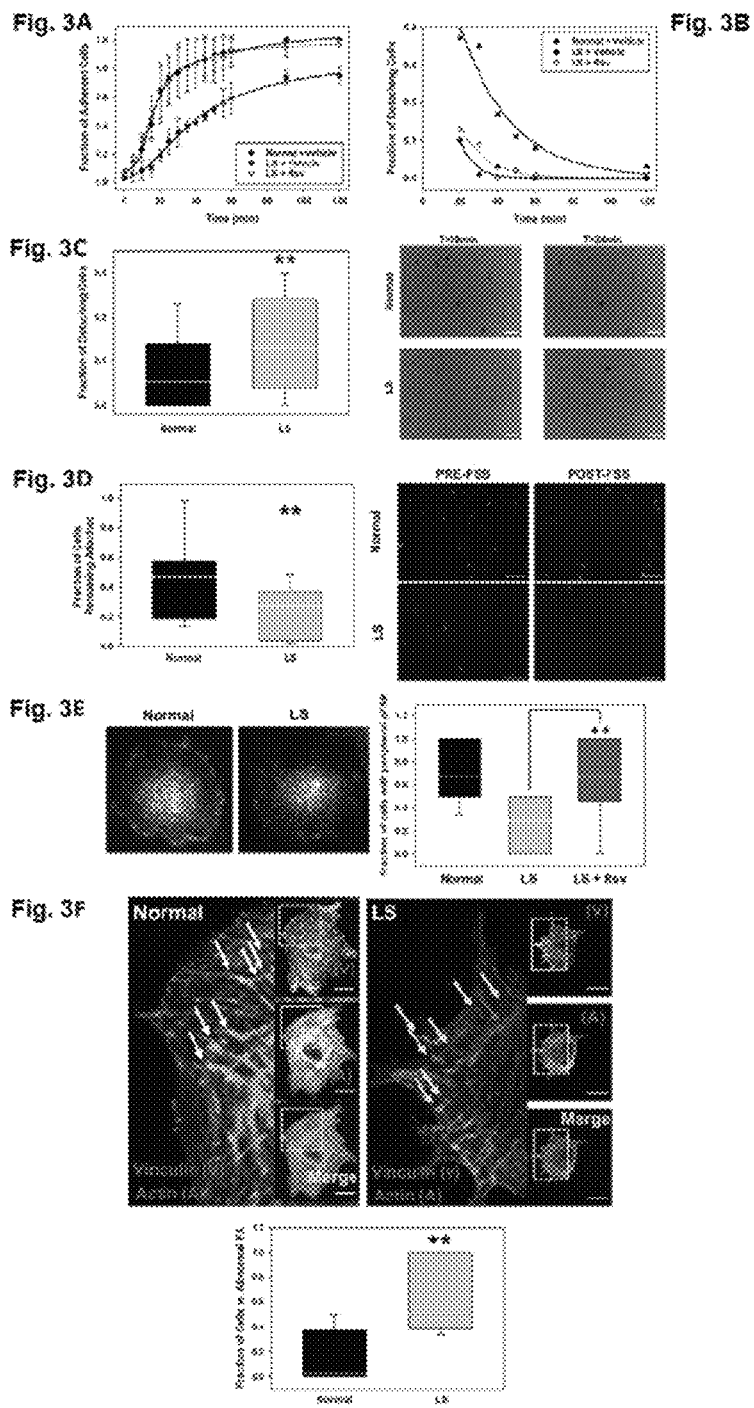
FIG. 3. LS patient cells display adhesion defects.
Figure 4:
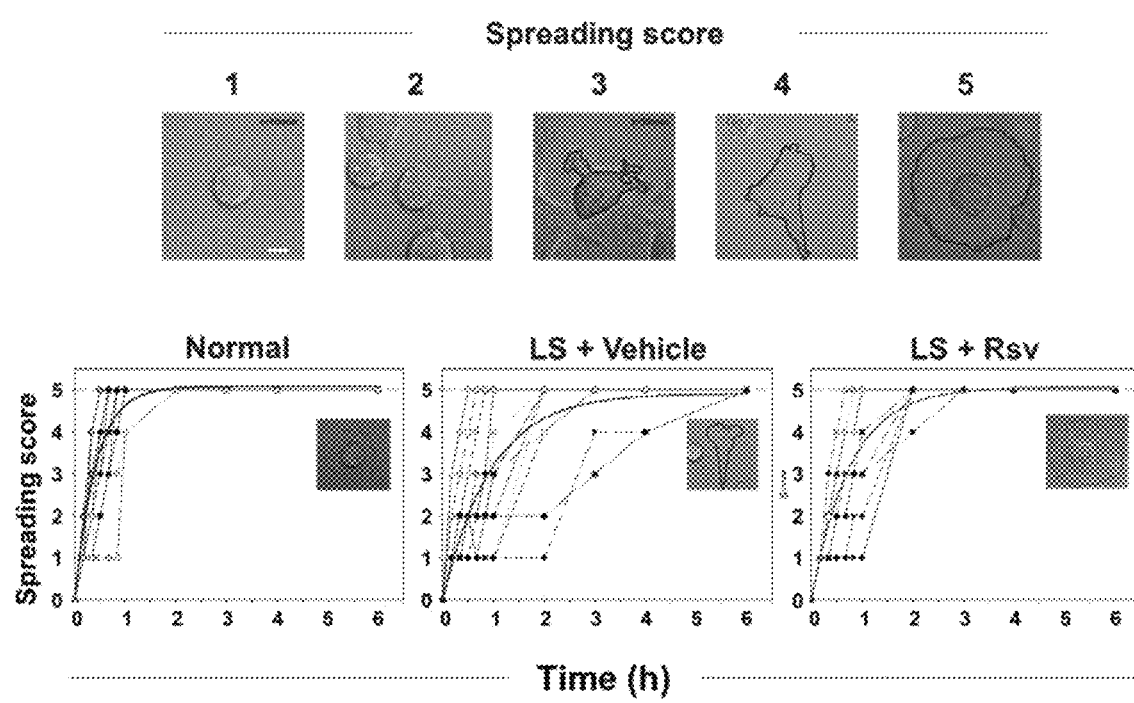
FIG. 4. LS patient cells display a cell spreading delay independent of their adhesion phenotype. Normal and LS patient cells (treated or not with vehicle or rosuvastatin (Rsv)) were seeded on fibronectin-coated surfaces and monitored using time-lapse microscopy. Time=0 was the moment in which the cells stably attach. According to their morphological characteristics, cells were scored following the 1-5 spreading score and exemplified by DIC images in the upper panel (perimeter of some cells is traced for better visualization). Time required to achieve each score level was recorded for 43-45 cells (note that many trajectories overlap) of each sample in three independent experiments and plotted as shown in the lower panels. A regression curve describing overall behavior is included (times required to reach half spreading trajectory are collected in Table I). Examples of the morphologies acquired by fully spread cells are also exemplified in the graph insets. Scale bar: 10 µm.

A von Bertalanffy logistic model was adopted to fit the data presented in FIG. 3A (adhesion) and FIG. 4 (spreading) as shown in Table 3. The estimated time to achieve half the maximal value of each process ($T_{0.5}$) was obtained and used to calculate continuous rates (K) according to: $K = -Ln(0.5)/T_{0.5}$. The associated error $\Delta K$ was estimated using standard rules of error propagation based on the determined $T_{0.5}$ error ($\Delta T_{0.5}$), according to $\Delta K = K(\Delta T_{0.5}/T_{0.5})$.

TABLE 3

| | Adhesion and Spreading Rates | | |
| --- | --- | --- | --- |
| | Process Continuous Rate(min$^{-1}$ × 10$^3$)$^a$ | | |
| Process | Normal | LS | LS + Rsv |
| Adhesion | 41 ± 2 | 17 ± 3** | 35 ± 5 |
| Spreading | 30 ± 2 | 17 ± 2** | 24 ± 2 |

$^a$Kinetic data from FIG. 3A (adhesion) and FIG. 4 (spreading) were fit using a non-linear regression model to estimate the continuous rates of each process for the indicated samples (see Materials and methods under Statistical analysis).
**indicates a significant difference between LS and Normal rates with p < 0.05 by the student's t-test.

Example 1

This example demonstrates the RhoGTPase modulators affect Low Syndrome (LS) cell spreading and fluid-phase uptake (FPU) phenotype severity.

Cell spreading on fibronectin-coated surfaces of cells treated with RhoA modulators in comparison to untreated cells was observed. Cells were fixed and stained with fluorescently labeled-phalloidin after 30 min spreading time at 37° C. Following imaging, cell area measurements were performed.

Normal fibroblasts displayed a "LS-like" cell spreading phenotype (Coon et al. (2009), supra) upon treatment with a RhoA activator (FIG. 1A), while incubation with this chemical worsened the already impaired spreading ability of LS cells (FIG. 1B). However, the use of a RhoA inhibitor ameliorated the cell spread phenotype (FIG. 1B). Importantly, these observations were confirmed using cells from another unrelated LS patient (FIG. 8A) and kidney HK2 and HEK293T OCRL1$^{-/-}$ K.O. (knockout) cells (FIG. 8B and data not shown, respectively; as compared to their wild-type counterparts).

These results indicate that the RhoA/Rac1 imbalance in LS cells is the underlying cause of the cell spreading defect. Further, the results suggest that these phenotypes can be corrected using RhoA inhibitors.

In order to gain insight concerning the RhoA-dependent signaling pathways that trigger this LS phenotype, we used pharmacological inhibitors of two important RhoA-effectors: Rho-associated kinase (ROCK) and Myosin Light Chain Kinase (MLCK), while also using an inhibitor of p21 activated kinase (PAK), which acts downstream of Cdc42/Rac1, as a control (Meshki et al., PLoS One 10.1371/journal.pone.0025332 (Sep. 23, 2011); Totsukawa et al., J Cell Biol 150: 797-806 (2000)). We found that, in contrast to the ROCK-inhibitor fasudil, the MLCK-inhibitor ML-7 was able to mitigate the cell spreading phenotype (FIG. 1C). These results suggest that RhoA hyperactivation induces cell spreading abnormalities through the RhoA effector MLCK. These observations agree with previous reports that MLC phosphorylation by MLCK is involved in the regulation of actin rearrangement at the cell periphery (Totsukawa et al. (2000), supra; Totsukawa J Cell Biol 164: 427-439 (2004)).

Example 2

This example demonstrates that statins alleviate LS membrane remodeling phenotypes.

Figure 2A:
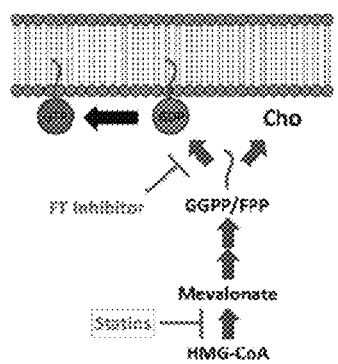
FIG. 2A. Scheme depicting point of inhibition of the statins and farnesyl-transferase (FT) inhibitors on the mevalonate pathway. Prenylated RhoGTPases are represented as membrane-anchored circles (blue and red for GDP- and GTP-loaded, respectively). HMG-CoA: 3-Hydroxy-3-Methyl-Glutaryl-CoA; GGPP: Geranylgeranyl Pyrophosphate; FPP: Farnesyl Pyrophosphate; Cho: cholesterol.

Statins decrease cholesterol (Cho) biosynthesis by inhibiting 3-hydroxy-3-methylglutaryl coenzyme A (HMG-CoA) reductase (FIG. 2A and McFarland et al., Int J Mol Sci 15: 20607-20637 (2014)); consequently, they also down-modulate the downstream synthesis of two intermediates (farnesyl-pyrophosphate and geranyl-geranyl-pyrophosphate) required for RhoA prenylation, which in turn is essential for GTPase membrane anchoring and activation (del Real et al., J Exp Med 200: 541-547 (2004); Demierre et al., Nat Rev Cancer 5: 930-942 (2005); and FIG. 2A). They also have been shown to be active against the RhoA hyperactivation observed in certain cancers (Zhong et al., Cancer Treat Rev 41: 554-567 (2015)).

Figure 2B:
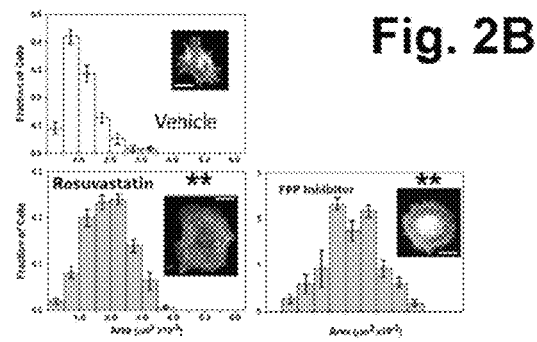
FIG. 2B. Histograms for LS patient cells treated with vehicle or the indicated drug were constructed as described and in FIG. 1. Insets show examples of stained cells representative of the high frequency groups within each histogram. Scale bar: 10 µm. **$p<(0.05/3=0.0167)$ (Bonferroni correction) by the KS test.

Several generation statins (Maji et al., Indian J Endocrinol Metab 17: 636-646 (2013)), including fluvastatin, atorvastatin, pitavastatin and rosuvastatin, were tested for their ability to ameliorate LS spreading defects. All statins mitigated to a certain extent the LS spreading phenotype; however, rosuvastatin produced the best results (rosuvastatin>pitavastatin>>>simvastatin and others) in terms of maximizing rescue effect over needed dose and toxicity (FIG. 2B and data not shown).

Figure 2C:
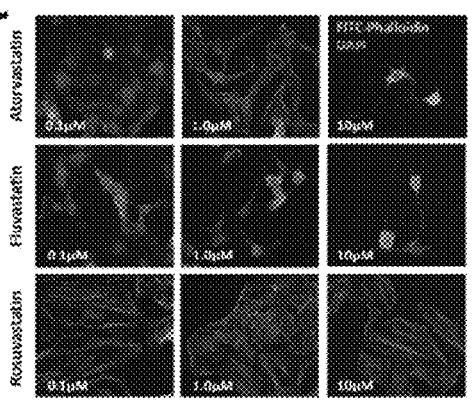
Figure 2E:
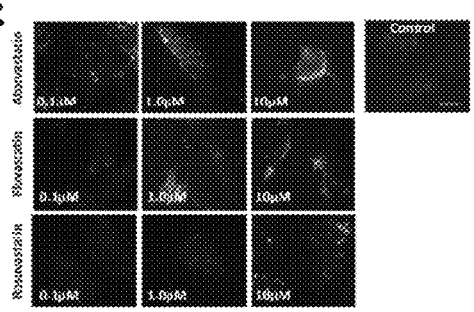

Phenotype alleviation was observed following the use of an acute rosuvastatin dose (100 µM for 1 h), but similar effect was also evident using lower concentrations (1-10 µM) sustained over longer periods of time (≥72 h; FIG. 2B). Importantly, the latter usage scheme better emulated currently approved treatment conditions with statins that render an effective concentration of free drug in plasma of up to 10 µM (Bjorkhem-Bergman et al., Br J Clin Pharmacol 72: 164-165 (2011)). Following exposure to statins, viability and stress-induced changes in morphology were determined for LS cells (FIG. 2C). Our results showed that rosuvastatin had minimal toxicity, while other statins including pitavastatin and cerivastatin were substantially toxic (FIG. 2C, D). It should be noted that the latter was recalled from the market due to severe rhabdomyolysis effects (Maji et al. (2013), supra). In addition, and to monitor the magnitude of the statins' effects on HMG-CoA reductase in LS cells, we incubated patient fibroblasts in Cho-free media supplemented with vehicle or statins and determined the uptake of fluorescently labeled Cho. While vehicle-treated cells had normal production of endogenous Cho, the ones exposed to statins (due to their HMG-CoA reductase inhibitory activity) were Cho-depleted at a different extent as evidenced by a substantial increase in the uptake of exogenous, fluorescently labeled Cho (FIG. 2E). Our results suggested that rosuvastatin in addition to being less toxic at the chronic dose, led to a less acute inhibition of cholesterol biosynthesis (and consequently to a lower demand of exogenous, fluorescent-analog uptake). However, in contrast with the relatively innocuous chronic exposure (10 µM for ≥72 h), we observed that acute doses of rosuvastatin (100 µM) induced toxicity when exposure time≥15 h (data not shown).

Example 3

This example demonstrates that statins alter RhoGTPase signaling but have no effect on LS ciliogenesis phenotype.

Figure 8:
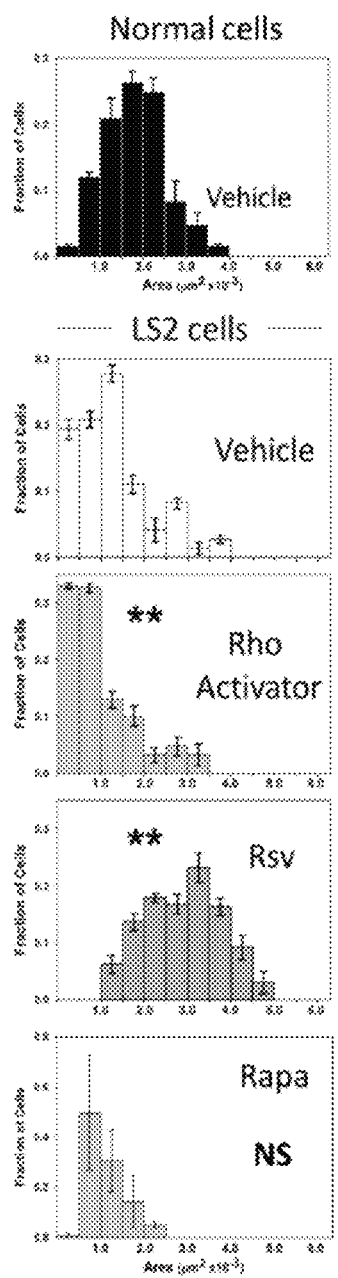
FIG. 8. Ocrl1-deficiency triggers a cell spreading phenotype in cells of different origin.
Figure 8:
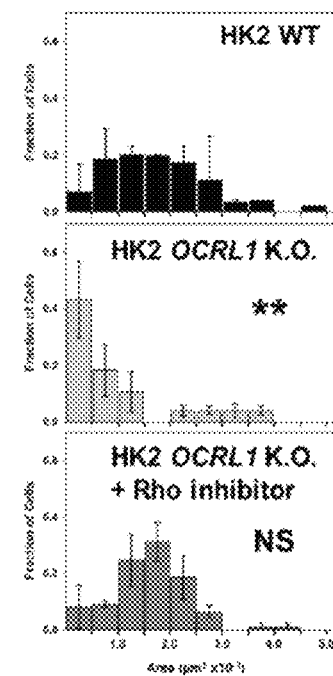
Figure 8:
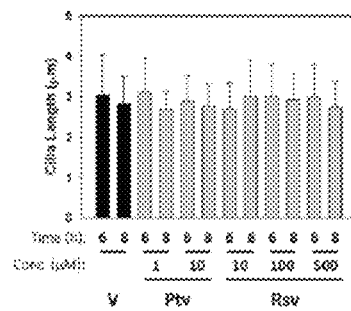
Figure 9:
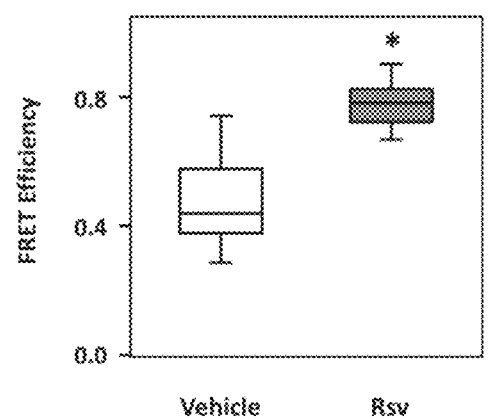
FIG. 9. LS treated with rosuvastatin displayed higher levels of activated Rac1 than vehicle-treated cells. LS patient cells expressing Rac1 FRET probe were treated with vehicle or rosuvastatin, imaged and FRET signals analyzed by the ratiometric method (*p<0.05, Wilcoxon test).

Statins inhibit isoprenoid chain biosynthesis (McFarland et al. (2014), supra; FIG. 2A); therefore, they impair the prenylation of RhoGTPases and their activation. In consequence, statin treatment is expected to lower all RhoGTPase activation levels. Since LS cells present a RhoA hyperactivation scenario (with consequent low levels of activated Rad), statins were tested for their ability to lower all RhoGTPase activation levels and relieve the suppression of Rac1 signaling. Statins were able to correct different forms of the membrane remodeling phenotype, i.e., cell spreading and FPU abnormalities (FIG. 2B and FIG. 2F). Importantly, the cell spreading phenotype observed in cells from another LS patient was also ameliorated by rosuvastatin (FIG. 8A). Further, using a validated FRET-based biosensor (Itoh et al., Mol Cell Biol 22: 6582-6591 (2002)), we determined that Rac1 activation levels were raised in LS cells upon rosuvastatin treatment (FIG. 9). We further demonstrated that a farnesylation inhibitor can mitigate the LS membrane remodeling defect and rescue the cell spreading phenotype of LS patient cells (FIG. 2B). Although able to revert LS membrane remodeling defects, statins were unable to mitigate PC assembly defects in LS patient cells (FIG. 8C). This observation further supports the idea that Ocrl1 acts on the cellular processes of membrane remodeling and ciliogenesis via different biochemical pathways.

Example 4

This example demonstrates that LS cells exhibit adhesion and spreading defects alleviated by statins.

To better characterize the LS cell spreading phenotype and statin's suppression mechanism, cell behavior was monitored using time-lapse microscopy. Specifically, cell spreading assays of normal and LS cells treated with vehicle or rosuvastatin were performed in real time by continuous imaging using Cytosmart devices (FIG. 3A) or at regular intervals in labtek chambers (FIG. 3B). The results indicated two major differences between normal and LS fibroblasts—cell adhesion and spreading capabilities.

Figure 10A:
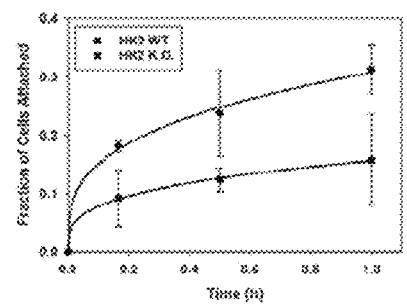
FIG. 10A and FIG. 10B. Human HK2 kidney cells WT and OCRL1 K.O. were used for adhesion (FIG. 10A) and ciliogenesis (FIG. 10B) assays.

While 80% of normal cells made stable adhesions by 30 minutes, even after one hour a substantial number of LS cells did not adhere or made unstable attachments (FIG. 3A and FIG. 3B). Analysis of this kinetic data highlighted differences in the rates of adhesion between normal and LS cells (Table I). Further, and in contrast with normal cells, a substantial number of LS fibroblasts established weak adhesions as evidenced by frequent LS cell de-attachments (FIG. 3B). A similar result was obtained when HK2 human proximal tubule cells OCRL1 K.O. were compared to HK2WT cells (FIG. 10A, upper panel).

Although RhoA is required for adhesion and migration (Kaibuchi et al., Ann Rev Biochem 68: 459-486 (1999)), Rac1 activation is required for cell adhesion consolidation (Lawson et al., Small GTPases 10.4161/sgtp.27958 (Mar. 7, 2014). To determine if a RhoA/Rac1 imbalance was responsible for LS adhesion defects, further assays were conducted. Normal cells treated with a RhoA-activator to emulate LS signaling unbalance displayed an increased proportion of de-attaching cells (data not shown). Importantly, rosuvastatin treatment alleviated the LS cell adhesion defect (FIG. 3A and FIG. 3B). This observation is also consistent with the effect of statins in counteracting RhoA hyper-activation in LS cells, enhancing Rac1 signaling.

Further, LS cells were more susceptible to de-attachment than normal cells when subjected to fluid sheer stress (FSS) exerted by rinsing with PBS 20 min after seeding cells on fibronectin-coated surfaces. Cell adhesion was monitored by time-lapse microscopy (FIG. 3C) and by fixing, actin staining and comparing the proportion of attached cells before and after exerting FSS (FIG. 3D).

Interestingly, focal adhesions showed a distinct organization in normal vs. LS cells, with the latter exhibiting less peripherally activated Focal Adhesion Kinase (FAK) as detected by immunofluorescence using an anti-phospho-Tyr$^{397}$ FAK antibody. This abnormality was alleviated by incubation with rosuvastatin (FIG. 3E). A similar result was observed in HK2 OCRL1$^{-/-}$ as compared to WT cells (FIG. 10A, lower panel). Importantly, these abnormalities were also alleviated by incubation with rosuvastatin (FIG. 3E, right panel). In addition, shorter, less mature vinculin-positive structures with decreased anchoring of stress fibers in LS cells were observed (FIG. 3F).

LS cells also took longer to reach a fully spread morphology as compared to their normal counterparts (FIG. 4). Time lapse microscopy was used to track the spreading status of individual cells by assigning them a "spreading score" (FIG. 4) as a function of spreading time. Briefly, a cell was considered as stably attached when it substantially decreased its x-y movements and needle-like filopodia structures became visible. With this data the time-course of evolution from initial to fully spread morphology of normal vs. LS cells was plotted (FIG. 4). While conventional spreading assays report a composite of both Rac1-dependent adhesion and spreading defects, time lapse-microscopy allowed the separate evaluation of one from another phenotype.

Spreading time T for each cell was computed with respect to the moment in which they were able to stably attach to the fibronectin-coated coverslip. In average it took a significantly longer time for LS than normal cells to stably attach (i.e., different attachment time); however, this moment was set to be spreading time T=0. Therefore, the spreading ability of each cell was evaluated independently of their initial adhesion capability. While most normal cells were fully spread, i.e., exhibited no further significant change in spreading area by 2 h after attachment, LS fibroblasts took longer or never reached such ultimate spread morphology (FIG. 4). The corresponding rates of spreading were calculated and collected in Table I. Importantly, in agreement with their ability to support Rac1-mediated spreading (Kou et al., J Biol Chem 284: 14734-14743 (2009)), statins also alleviated this deficiency (FIG. 4).

Example 5

This example demonstrates that rapamycin mitigates PC assembly defects in LS patient cells.

Figure 5:
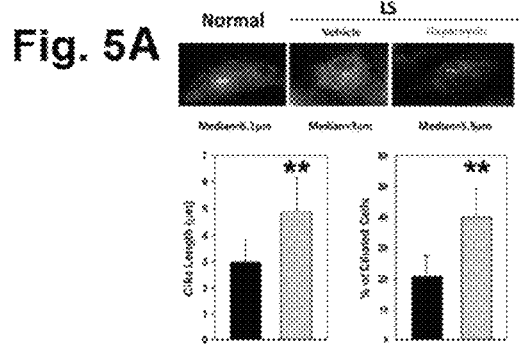
FIG. 5. LS patient cells display hyperactivation of the mTOR signaling pathway.
Figure 5:
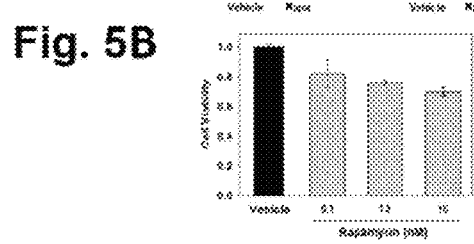
Figure 5:
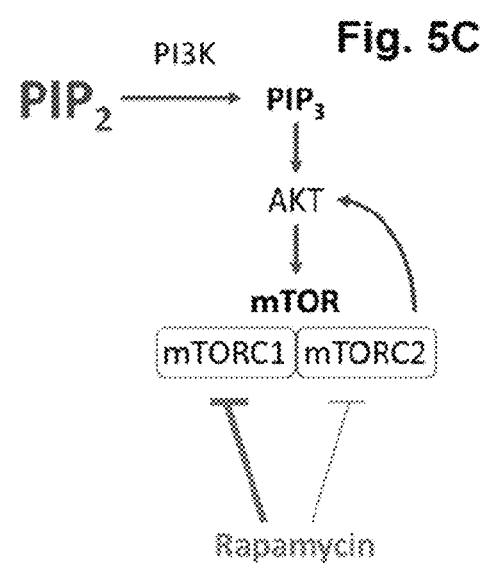
Figure 5:
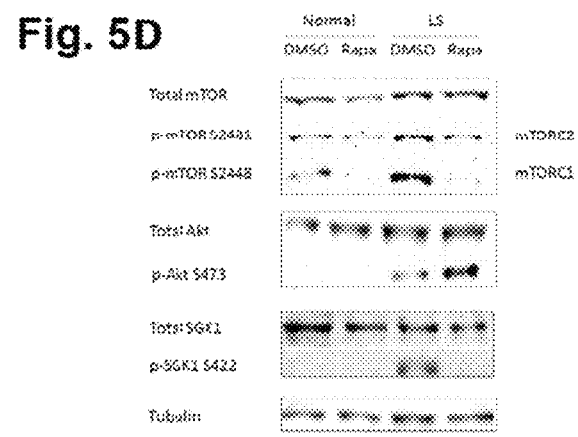
Figure 5:
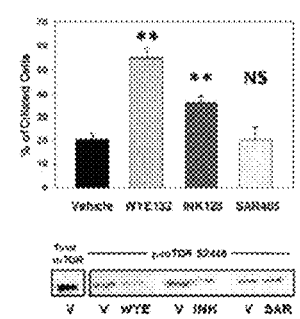

Since statins could not correct LS ciliogenesis abnormalities, drugs known to mitigate PC phenotypes in ciliopathies were examined. Rapamycin is currently in clinical trials for the treatment of polycystic kidney disease and has also shown promise against Bardet-Biedel's syndrome (Braun et al., Clin J Am Soc Nephrol 9: 881-888 (2014); Tobin et al., Pediatr Nephrol 23: 2095-2099 (2008); Shillingford et al., J Am Soc Nephrol 23: 1674-1681 (2012); Stallone et al., Nephrol Dial Transplant 27: 3560-3567 (2012); and Jimeno et al., J Clin Oncol 26: 4172-4179 (2008)). Therefore, this drug was tested as a candidate for mitigation of LS ciliogenesis defects. Results showed that LS fibroblasts treated with rapamycin showed a significant increase in the PC length and fraction of ciliated cells in comparison to the vehicle-treated group (FIG. 5A). Specifically, PC phenotype alleviation capabilities were observed under both acute treatments: 100 nM for 12 h and under a more sustained treatment regime (≥72 h) at a concentration compatible with plasma levels yielded by current approved rapamycin treatments, i.e., 10 nM (Jimenco et al. (2008), supra) (FIG. 5). The toxicity on LS cells associated with the use of this drug was found to be minimal (≤10-15% decrease after 72 h-treatment; FIG. 5B); while this drug had no effect on ciliogenesis by normal cells (data not shown).

In addition, we established that rapamycin was unable to alleviate membrane remodeling abnormalities (FIG. 8A, bottom panel); once again, further supporting the idea that membrane remodeling and PC phenotypes are caused by distinct mechanisms.

Example 6

This example demonstrates that LS cells display constitutive activation of the mTOR pathway that can be mitigated by rapamycin.

The activation of the Akt and mTOR signaling pathways in LS cells treated or not with rapamycin was examined. Cell lysates were prepared, resolved by SDS-PAGE and the presence of phosphorylated and dephosphorylated key elements of the Akt and mTOR pathways were investigated by Western blotting with specific antibodies (FIG. 5D).

Figure 10B:
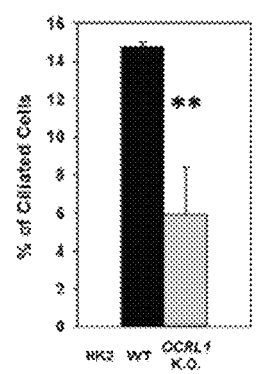
Figure 10:
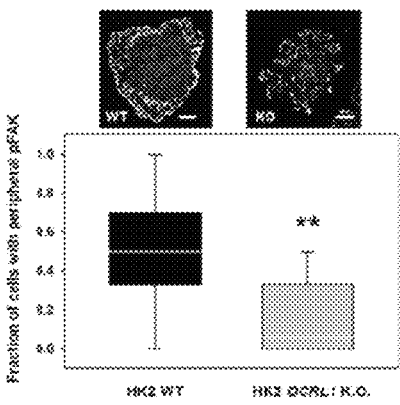
FIG. 10. Ocrl1-deficiency triggers adhesion and ciliogenesis phenotypes in human kidney HK2 cells.
Figure 10:
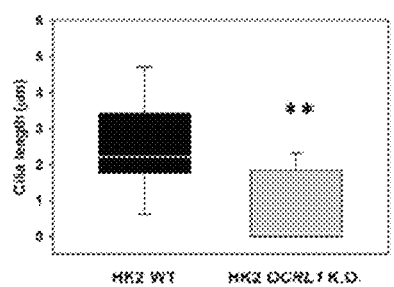
Figure 10C:
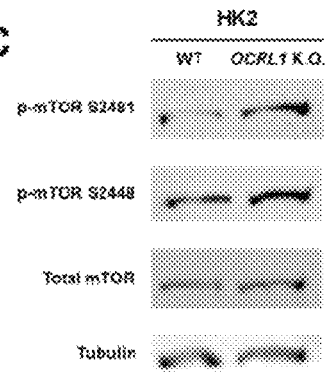
FIG. 10C. Levels of activated mTOR in WT and OCRL1 K.O. cells were probed as in FIG. 1.
Figure 11:
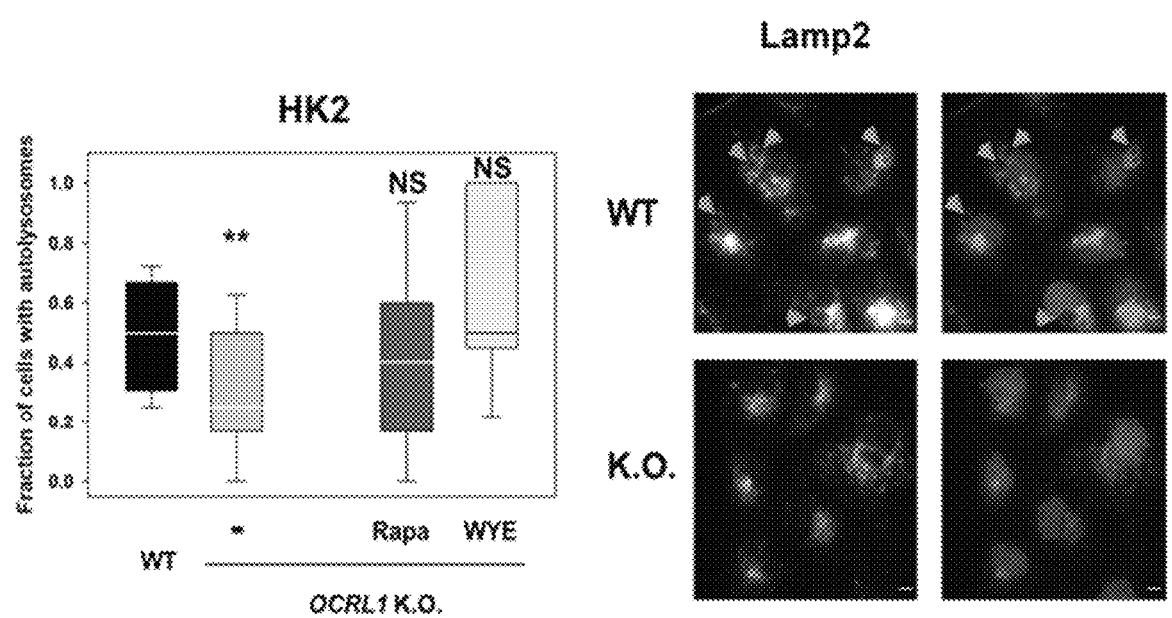
FIG. 11. Absence of Ocrl1 led to autolysosome deficiencies in human kidney HK2 cells that can be rescued by the mTOR inhibitors rapamycin and WYE. Human HK2 kidney cells WT and OCRL1 K.O. were stained for Lamp2 by immunofluorescence and treated or not with rapamycin (10 nM) or WYE (1 μM). Fraction of cells displaying these structures were quantified for each experimental group and statistically analyzed using the Wilcoxon test applying the Bonferroni correction for 3 comparisons of 3 OCRL1 K.O. samples vs. their WT counterpart, **: p<(0.05/3=0.016667); NS: non-significant. Representative images of analyzed cells are shown on the right, arrows point to some typical autolysosomes (Lamp2: green; DAPI: blue). Scale bar: 10 μm.

In contrast to normal cells, the PI3K/Akt pathway was constitutively activated in LS cells as inferred by the presence of Akt phosphorylated at Serine 473 (FIG. 5D). Importantly, both mTOR protein complexes mTORC1 and mTORC2 were activated in LS above the levels of normal cells (FIG. 5D) and downstream kinase SGK1 was found to be phosphorylated at serine 422 (FIG. 5D), which is consistent with activation of this enzyme (Garcia-Martinez et al., Biochem J 416: 375-385 (2008)). Band densitometry (followed by normalization by total amount of protein) of at least 3 experiments revealed that in LS cells phosphorylated AKT, SGK1 and mTORC1 levels were about twice more abundant than in normal cells (a more modest 20-50% increase was noted for phosphorylated mTORC2). Similar results were obtained by using HK2 WT and HK2 OCRL1$^{-/-}$ lysates (FIG. 10B and FIG. 10C).

mTOR and SGK1 activation in LS cells was counteracted by rapamycin treatment (FIG. 5D) and activation of the upstream PI3K/Akt pathway was not affected by exposure to this drug. To further confirm that counteracting mTOR pathway hyperactivation was responsible for re-establishing ciliogenesis in LS cells (and not an off-target/side effect of rapamycin) different mTOR inhibitors (INK128 and WYE132) that, in contrast to rapamycin, act via a non-competitive/allosteric mechanism were used (Zhang et al., Apoptosis 20: 50-62 (2015); and Yu et al., Cancer Res 70: 621-631 (2010)). Importantly, both INK128 and WYE132 were able to decrease mTOR phosphorylation and, very importantly, to rescue ciliogenesis defects in LS cells (FIG. 5E). In contrast, inhibition of PI3K cIII (this PI3K class is unable to activate mTOR (Ronan et al., Nat Chem Biol 10: 1013-1019 (2014); Jaber et al., PNAS USA 109: 2003-2008 (2012); and Juhász et al., J Cell Biol 181: 655-666 (2008)) with SAR405 did not affect mTOR activation and had no effect on ciliogenesis by LS cells (FIG. 5E). Hyperactivation of mTOR is expected to inhibit autophagy, which is of great importance for kidney proximal tubule cells (Havasi et al., Semin Nephrol 36: 174-188 (2016); Livingston et al., Semin Nephrol 34: 17-26 (2014); Jian et al., Kidney Int 82: 1271-1283 (2012); Kimura et al., J Am Soc Nephrol 22: 902-913 (2011); and Takabatake et al., Nephrol Dial Transplant 29: 1639-1647 (2014)), a subpopulation known to be affected in LS patients (Oltrabella et al., PLoS Genet 10.1371/journal.pgen.1005058 (Apr. 2, 2015); Vicinanza et al., EMBO J 30: 4970-4985 (2011); Recker et al., Pediatr Nephrol 30: 931-943 (2015); Bockenhauer et al., Clin J Am Soc Nephrol 3: 1430-1436 (2008); Laube et al., Arch Dis Child 89: 479-480 (2004); Loi, Orphanet J Rare Dis doi.org/10.1186/1750-1175-1-16 (May 18, 2006); and Hsieh (2018), supra). Indeed, the fraction of cells displaying autolysosomes was substantially decreased in HK2 human proximal tubule OCRL1 K.O. than in WT cells (FIG. 11). This phenotype was suppressed by treatment of the cells with mTOR inhibitors (FIG. 11).

Example 7

This example demonstrates that the combination of rosuvastatin and rapamycin mitigated both membrane remodeling and PC assembly phenotypes.

Figure 6:
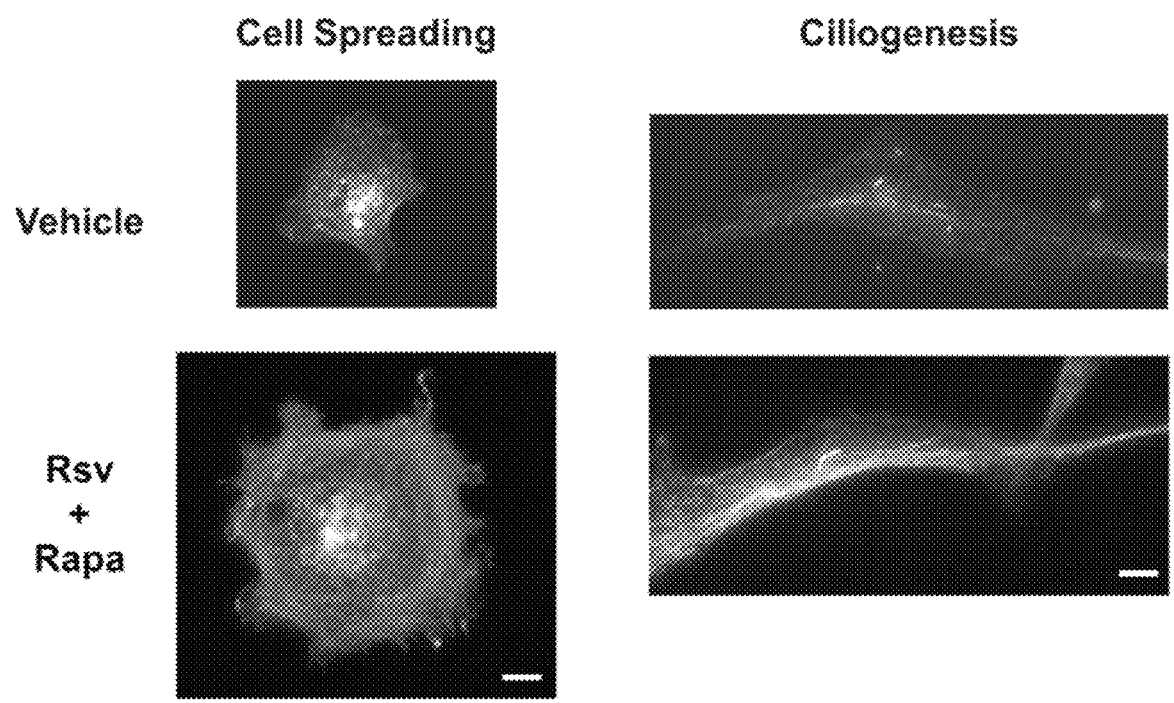
FIG. 6. Treatment with combination of rapamycin and rosuvastatin ameliorate both ciliogenesis and spreading phenotypes in LS patient cells. LS cells were treated with either Rapa or Rsv or a combination of both and subjected to cell spreading and ciliogenesis assays.
Figure 7:
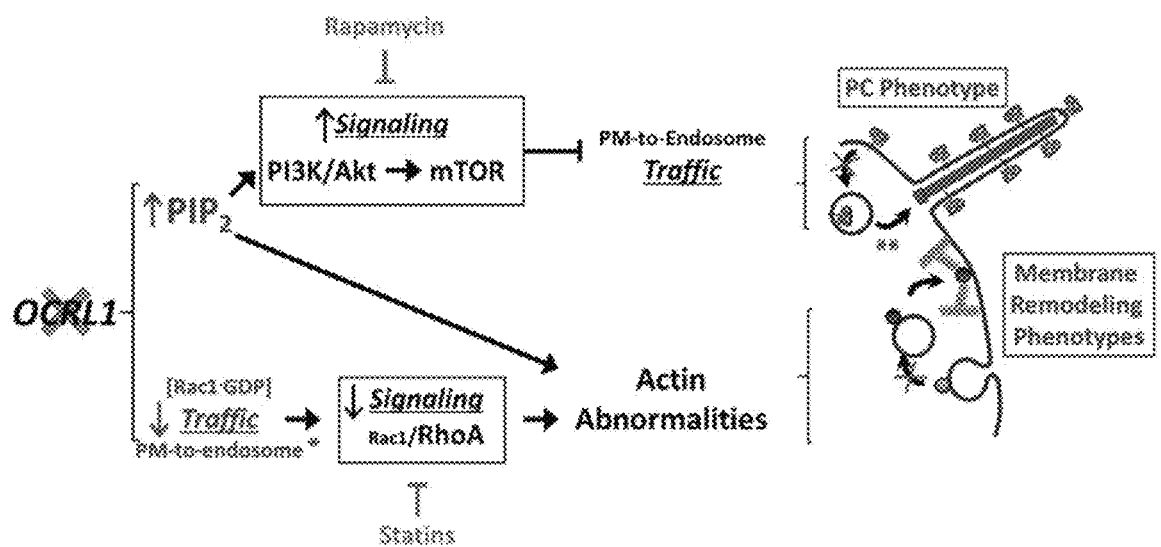
FIG. 7. Working model for LS phenotype development due to Ocrl1 lack of activity. Ocrl1 deficiencies would increase the availability of the PI3K substrate PIP2 leading to mTOR hyperactivation and consequently to inhibition of cilia-localized cargo traffic to endosomes and their delivery to the cilia (** Coon et al. (2012), supra). Indeed, PIP2 accumulation will also interfere with normal actin dynamics affecting membrane remodeling processes. Ocrl1 abnormal function is also directly linked to vesicle trafficking defects and [Rac1-GDP] requires traffic to endosomes to be activated by the GEF TIAM (* Palamidessi et al., Cell 134: 135-147 (2008); and Barbieri et al., Curr Opin Cell Biol 39: 21-27 (2016)) and recycle back to the plasma membrane (PM) to promote membrane rearrangements.

Since results suggested that Ocrl1's roles in membrane remodeling and PC assembly are independent and mediated by distinct signaling pathways, RhoGTPase-dependent and mTOR-dependent, respectively, we tested a combination treatment of LS cells with statins and rapamycin to determine if both are needed to rescue both phenotypes simultaneously. Significant rescue of both phenotypes in LS (Ocrl1 NULL) cells incubated with a mix of rosuvastatin and rapamycin was observed (FIG. 6). No obvious effect of rapamycin or rosuvastatin on normal cells was detected (i.e., no increase on ciliogenesis or spreading of normal cells).

All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

The invention illustratively described herein may be suitably practiced in the absence of any element(s) or limitation(s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" includes one or more methods and/or steps of the type, which are described herein and/or which will become apparent to those ordinarily skilled in the art upon reading the disclosure.

The terms and expressions, which have been employed, are used as terms of description and not of limitation. In this regard, where certain terms are defined under "Definitions" and are otherwise defined, described, or discussed elsewhere in the "Detailed Description," all such definitions, descriptions, and discussions are intended to be attributed to such terms. There also is no intention in the use of such terms and expressions of excluding any equivalents of the features shown and described or portions thereof. Furthermore, while subheadings, e.g., "Definitions," are used in the "Detailed Description," such use is solely for ease of reference and is not intended to limit any disclosure made in one section to that section only; rather, any disclosure made under one subheading is intended to constitute a disclosure under each and every other subheading.

It is recognized that various modifications are possible within the scope of the claimed invention. Thus, although the present invention has been specifically disclosed in the context of preferred embodiments and optional features, those skilled in the art may resort to modifications and variations of the concepts disclosed herein. Such modifications and variations are considered to be within the scope of the invention as claimed herein.

What is claimed is:

1. A combination of active agents for the treatment of Lowe Syndrome, which combination comprises rosuvastatin and rapamycin in amounts sufficient to treat Lowe Syndrome therapeutically.

2. A pharmaceutical composition comprising the combination of claim 1 and a pharmaceutically acceptable carrier.

3. A combination of pharmaceutical compositions comprising a first pharmaceutical composition comprising rosuvastatin in an amount sufficient to treat Lowe Syndrome (LS) therapeutically and a pharmaceutically acceptable carrier and a second pharmaceutical composition comprising rapamycin in an amount sufficient to treat LS therapeutically and a pharmaceutically acceptable carrier.

4. The combination of pharmaceutical compositions of claim 3, in which the first and second pharmaceutical compositions are formulated to be administered by the same or different routes.

5. A method of treating a patient for Lowe Syndrome (LS), which method comprises administering to the patient:
    (i) a combination of claim 1;
    (ii) a pharmaceutical composition comprising the combination of claim 1 and a pharmaceutically acceptable carrier; or
    (iii) a combination of pharmaceutical compositions comprising:
        (a) a first pharmaceutical composition comprising rosuvastatin in an amount sufficient to treat LS therapeutically and a pharmaceutically acceptable carrier, and (b) a second pharmaceutical composition comprising rapamycin in an amount sufficient to treat LS therapeutically and a pharmaceutically acceptable carrier.

\* \* \* \* \*